United States Patent [19]

Yang et al.

[11] 4,223,164
[45] Sep. 16, 1980

[54] ETHOXYLATION WITH STRONTIUM BASES

[75] Inventors: Kang Yang; Gerald L. Nield; Paul H. Washecheck, all of Ponca City, Okla.

[73] Assignee: Conoco, Inc., Ponca City, Okla.

[21] Appl. No.: 54,089

[22] Filed: Jul. 2, 1979

[51] Int. Cl.² ............................................. C07C 41/02
[52] U.S. Cl. .................................. 568/618; 568/613; 568/622; 568/678
[58] Field of Search ................ 568/618, 613, 622, 678

[56] References Cited

U.S. PATENT DOCUMENTS

3,328,306  6/1967  Ellis ................................. 568/618 X

Primary Examiner—Howard T. Mars
Attorney, Agent, or Firm—Cortlan R. Schupbach, Jr.

[57] ABSTRACT

Basic compounds of strontium catalyzed the ethoxylation of alcohols in the presence of phenol or alkylphenol co-catalyst. Strontium-produced ethoxylates have sharper ethylene oxide distributions, lower free alcohol, lower pour points, and better detergency than the ethoxylates obtained from alkali base catalysis.

11 Claims, 11 Drawing Figures

ETHOXYLATION WITH STRONTIUM BASES

This invention relates to the production of ethoxylated alcohols by reacting said alcohols with ethylene oxide. More particularly, this invention relates to the production of ethoxylated alcohols by reacting said alcohols in the presence of a basic strontium compound as catalyst promoted by phenol or alkylated phenols.

The general reaction of alcohols and ethylene oxide to form ethoxylated alcohols or ethylene oxide adducts has long been known and practiced on a commercial scale. For example, these ethylene oxide adducts have been used as detergents and cleaning agents, domestic and industrial laundry detergents, detergent builders, polishers, sanitizers, and dry cleaning materials. Other users include the pulp and paper industry and the fiber industry. These materials are especially adapted to these uses since they have functional properties such as wetting power, foaming, emulsifying, and dispersing abilities as well as solubilization and detergent abilities.

Much literature is available in the general area of ethoxylation of alcohols. Many references are also available relating to the catalytic ability of various materials and the mechanism and kinetics of these reactions. For example, French Pat. No. 1,365,945 teaches the use of compounds containing an active hydrogen atom reacted with ethylene oxide in the presence of an alkali metal base.

Acidic catalysts in general are also known. However, the ethoxylation of alcohols inevitably produces a distribution of various adducts. For example, on surfactant applications an adduct of too few ethylene oxide molecules is not effective because of poor solubility, while an adduct with too many ethylene oxide molecules is likewise undesirable because surface tension reduction per unit mass decreases drastically with increasing molecular weight. Thus it has long been essential to produce and use ethoxylates with as sharp a distribution in the desired mole adduct range (5 to 10 usually) as possible. Acid catalyzed reaction such as that described above produces such ethoxylates, but these catalysts produce some harmful side products such as dioxanes which must be separated and removed prior to use.

Russian Pat. No. 523,074 teaches that alkali metal and various carbonates can be used to catalyze this reaction. The side product formation in these base catalyzed reactions is very low, but in base catalyzed reactions the adduct distribution is undesirably broad such that a large proportion of the product obtained is not useful.

Representative of but not exhaustive of the art in this area is U.S. Pat. No. 3,328,467 which describes the use of zeolites and modified zeolites as catalysts in the ethoxylation reactions. French 1,557,407 uses triethyl oxonium fluoroborate to catalyze such reactions. Indeed, the art abounds with references to alkali metal hydroxide such as sodium and potassium hydroxide, tertiary amines, and sodium metal. German Offenlegungsschrift No. 2,639,564 teaches polyalkylation of active hydrogen compounds in the presence of sodium fluoroborate or perchlorates of metal such as magnesium, calcium, manganese or zinc. U.S. Pat. No. 3,969,417 uses tertiary oxonium salts as a catalyst.

U.S. Pat. No. 3,830,850 describes adding sodium, potassium, lithium, rubidium, cesium, calcium, barium, or strontium to condense phenols with formaldehyde, then adding ethylene oxide in an ethoxylation reaction. However, all these materials have the disadvantages described and set forth above.

The catalyst which provides low by-product levels of base catalyst yet has the narrow distribution of the preferred mole adducts obtained from acid catalysts would be of great benefit. Such a catalyst would promote the narrowing of the product distribution curve and would contribute significantly to the intrinsic value of the ethoxylate produced. Such a catalyst is described in U.S. application Ser. No. 916,421 filed June 6, 1978. However, this catalyst has an induction period ranging up to about 20 minutes at 178° C. and produces from 1 to 2 percent polyethylene glycol in the product. In addition, this catalyst is a metal which while generally accepted as safe, should be avoided in continuous contact. For example, barium hydroxide described as a catalyst in this application is often used for additional purposes such as clarifying x-rays when taken internally. This material, however, should be used only under medical supervision in such large amounts and continued exposure should be avoided.

It is therefore an object of the present invention to provide a catalyst system which will yield a narrow high mole adduct distribution from the reaction of alcohols of all classes with ethylene oxide while providing low levels of undesirable by-products and unreacted free alcohol while providing a reaction which is immediately effective with reduced induction period. Other objects will become apparent to those skilled in this art as the description proceeds.

It has now been discovered according to the instant invention that ethoxylation of all classes of alcohols and preferably alkanols can be carried out in the presence of strontium bases such as strontium oxide, hydrated strontium oxide, and strontium hydroxide to produce a narrow distribution of ethylene oxide adducts while yielding a very low level of free alcohols and undesirable by-products. The catalyst also reduces the previously noticed induction period before the ethoxylation reaction begins. These benefits are obtained by adding to the catalyst system an effective amount of a catalyst promoter comprising phenol, alkylated phenols, or mixtures of these, said phenols having the general formula wherein $R^1$, $R^2$, $R^3$, $R^4$, and $R^5$ are, independently, hydrogen or an alkyl group containing from 1 to 16 carbon atoms. Use of alkyl groups containing from 1 to 10 carbon atoms is preferred.

The instant invention describes a method for the ethoxylation of alcohols comprising contacting said alcohols with ethylene oxide in the presence of strontium base catalyst together with an effective amount of phenol or alkyl substituted phenol or mixtures of these to promote the reaction.

The instant invention can be carried out at temperatures of from about 90° C. to about 260° C. Normally, the alcohols reacted under the process of the instant invention will contain from about 4 to abut 24 carbon atoms, but alcohols containing from about 10 to about 18 carbon atoms are those most used for commercial purposes. The process of the present invention can be carried out at ambient pressures. However, pressures up to 100 pounds per square inch gauge (psig) can also be used but pressures below 60 psig are preferred. Pressures below ambient can be used.

Representative examples of materials which promote strontium base catalysts are phenol, ortho cresol, meta-cresol, para-cresol, 2,4-dialkylphenol, 2,5-dialkylphenol, nonyl phenol, octylphenol, 2,3,6-trialkylphenol, 2,4,6-trialkylphenol, 2,4,5-trialkylphenol, and phenol alkylated with alkylene oligomers such as propylene tetramer, propylene pentane, and butylene trimers.

While pressure or lack of pressure is not a detriment to the process of the intant invention, normally a pressure of up to about 100 pounds per square inch gauge (psig) can be used. Preferred pressures are from about 10 to about 50 psig. However, it must be realized that the reaction can be carried out at lower pressures or at pressures above 100 psig if desired. It is simply more convenient to carry out the reaction in the pressure range of from about atmospheric to 100 psig.

The instant invention is normally carried out at temperatures of from about 120° to about 260° C. However, for practical purposes, commercial operations will normally be carried in the temperature range of from about 150° C. to about 250° C. Temperatures in the range of from about 160° C. to about 190° C. are most preferred.

Reaction products can have any desired content of ethylene oxide but will normally range from about 30 to about 80% content of ethylene oxide (EO) based on weight. However, for most purposes, the content of ethylene oxide will range from about 40% to about 70% by weight. The amount of ethylene oxide present in the reaction is not critical other than the minimum amount necessary to provide sufficient units to reach the mole adduct level desired for the alcohols being reacted.

Strontium catalysts of the instant invention are basic catalysts which provide a sharp distribution as to the mole adducts formed while reducing greatly the amount of unreacted free alcohols and undesirable by-products normally found in sharp distribution reactions. That strontium is effective is surprising since of the prior art basic catalysts known, barium oxide when used alone will yield sharp distribution with lowered amounts of by-products but metal oxides of calcium, magnesium and strontium used alone show no significant ethoxylation activity. However, when the phenol or alkylated phenol co-catalyst is used with the basic strontium catalyst of the instant invention, the low induction period, highly selective reaction is obtained.

For purposes of the instant invention the strontium catalyst can be strontium oxide alone, strontium hydroxide, and strontium hydroxide hydrates. Any of these strontium compounds are effective in the process of the instant invention when used with phenol or substituted phenol co-catalysts in an effective amount. When used alone, these strontium bases are not effective. When used, these catalyst mixtures can be used in any desired quantity. The larger the quantity used, the more quickly the reaction goes to completion, although larger quantities do not appear to significantly alter the distribution obtained.

For practical purposes, normally from about 0.05 to about 5.0 weight percent strontium catalyst based upon the weight of the alcohol to be reacted would be present in the reaction. These catalysts are not significantly effective in the absence of the phenol or substituted phenol promoters. The amount of phenol or substituted phenol promoters which are present with the strontium catalyst is generally an effective amount. These effects of the promoters become significant at about 0.05 percent by weight based upon the weight of the alcohol to be reacted and increase with increasing amounts of phenol or substituted phenol co-catalyst added, although it is logical to expect an upper limit after which the amount of promoter present will produce no additional benefits.

Normally, these phenol and substituted phenol promoters will be added to the strontium catalyst in amounts ranging from about 0.05 to about 5.0 by weight based upon the weight of the alcohol to be reacted, although amounts ranging from about 0.15 to about 2.0 are preferred and amounts from about 0.3 to about 0.8 by weight are most preferred. It is very apparent, however, that these limits can vary substantially since the promoter is effective at all levels to some extent.

Representative examples of strontium containing catalysts are strontium oxide, $Sr(OH)_2$, and $Sr(OH)_2 \cdot XH_2O$ wherein X represents the number of water molecules present. X is not a critical number, but monohydrate and octahydrate are common commercial forms.

While the instant invention is effective with all classes of alkanols, primary, secondary, linear and branched, linear and branched primary alkanols are the most commonly used alcohols and are the preferred alcohols of the instant invention. Representative examples of such alcohols are those derived by hydrogenation of natural fats and oils, such as CO and TA alcohols, trademark of and sold by Proctor and Gamble Co., such as CO-1214 N alcohol, CO 1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be ethoxylated. Examples of these alcohols are ALFOL alcohols, trademark of and sold by Conoco Inc., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohols, trademark of and sold by Shell Oil Co., such as NEODOL 23 alcohol, NEODOL 25 alcohol, NEODOL 1418 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol. Guerbet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp.

Generally, useable alcohols include 1-decanol; 1-undecanol; 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol;

2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadedcanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol.

Generally the treatment of alcohols with ethylene oxide yields a non-ionic detergent since hydrogen bonding to numerous oxygen atoms makes the polyether end of the molecule water soluble. Alternatively, the ethoxylates can be converted into sulfates and used in the form of alkali metal salts.

The instant invention thus provides for the production of highly efficient alcohol ethoxylates from primary and secondary branched chain and straight chain alcohols, particularly alkanols, in a novel highly unexpected manner. The alcohols normally contain from about 4 to about 24 carbon atoms. The reaction products are useful as non-ionic surface active agents with high wetting powers and are composed of mixtures of mono-alkyl ethers of polyethylene glycol.

Thus in the preferred form of the instant invention, ethylene oxide is reacted with a branched chain or straight chain alkanol in the presence of strontium oxide, strontium hydroxide, or other strontium bases promoted by an effective amount of a phenol or substituted phenol or mixtures of these.

The invention is more concretely described with reference to the examples below wherein all parts and percentages are by weight unless otherwise specified. The examples are provided to illustrate the instant invention and not to limit it.

EXAMPLE 1

A 600 cubic centimeter (cc) stainless steel reactor was charged with 120 grams of ALFOL 1214 alcohol (Trademark of and sold by Conoco Inc.) and a catalyst. The catalyst was selected from the group consisting of barium hydroxide.$H_2O$ 0.3 grams, strontium hydroxide 0.8$H_2O$ 0.3 grams, or strontium oxide 0.3 grams. After purging the reactor with nitrogen at the rate of 500 cc per minute for 30 minutes at 150° C., the reactor was evacuated and the temperature was raised to 178° C. Ethylene oxide was introduced to a total pressure of 40 pounds per square inch gauge and EO uptake at this constant pressure was measured as a function of time. After ethoxylation, the base was neutralized with carbon dioxide.

Figure 1:
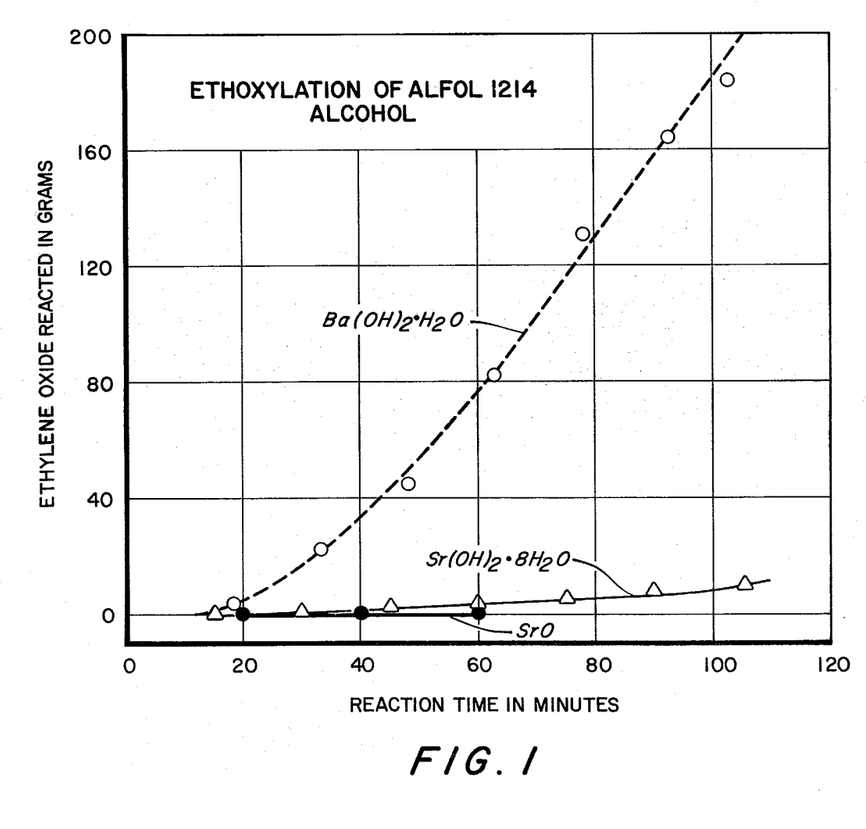

The results of the experiment showed that the barium containing catalyst was active whereas the strontium catalyst showed either no activity or activity which was detectible but not commercially significant. The results of this experiment are shown in FIG. 1.

EXAMPLE 2

Figure 2:
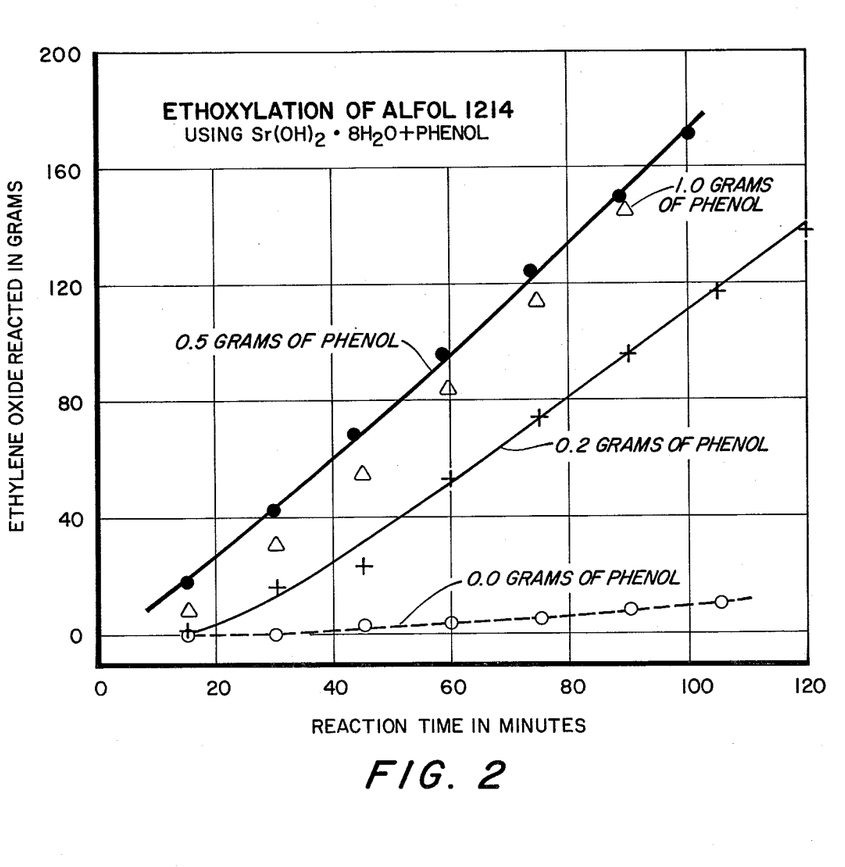

Further experiments were carried out as described in Example 1 using strontium hydroxide 0.8$H_2O$ in the presence of various amounts of phenol promoters. A promoter strongly activated the strontium containing catalyst to yield a significant ethoxylation reaction. The progress of this experiment is set forth in FIG. 2.

EXAMPLE 3

Figure 3:
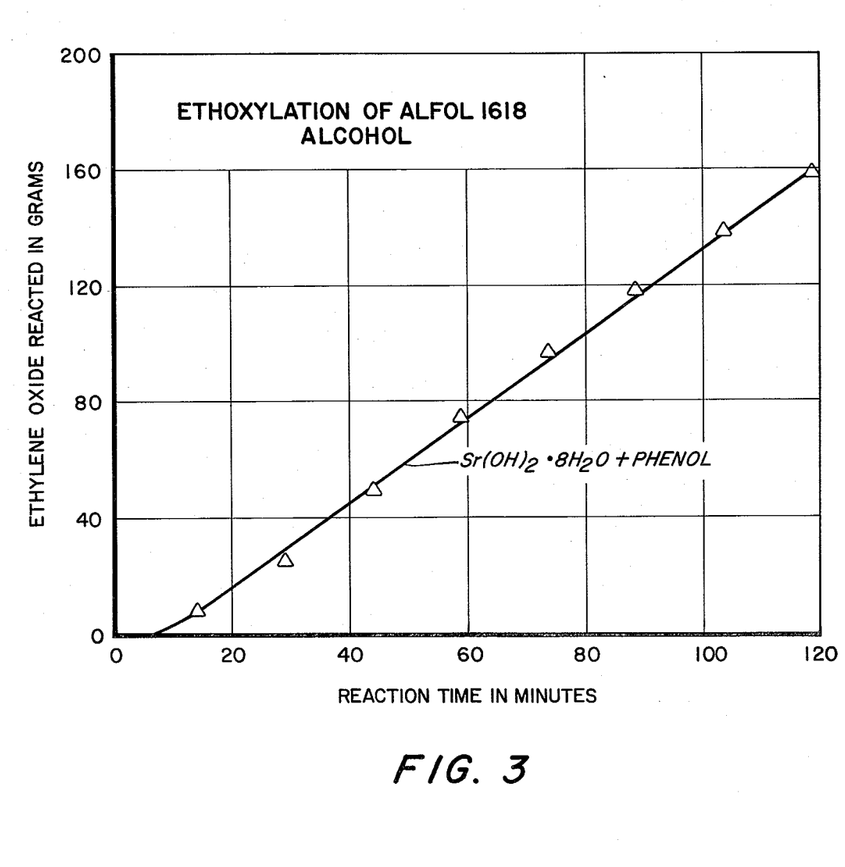

An experiment was performed as described in Example 1 using 120 grams of ALFOL 1618 alcohols (16 to 18 carbon containing alcohol trademark of and sold by Conoco Inc.) The catalyst comprising 0.3 grams of strontium hydroxide 0.$H_2O$ and 0.5 grams of phenols was used. The ethoxylation rate with a 16 to 18 carbon member alcohol was approximately that of the 12 to 14 carbon atoms alcohol of Example 2. The progress of this experiment is shown in FIG. 3.

EXAMPLE 4

Figure 4:
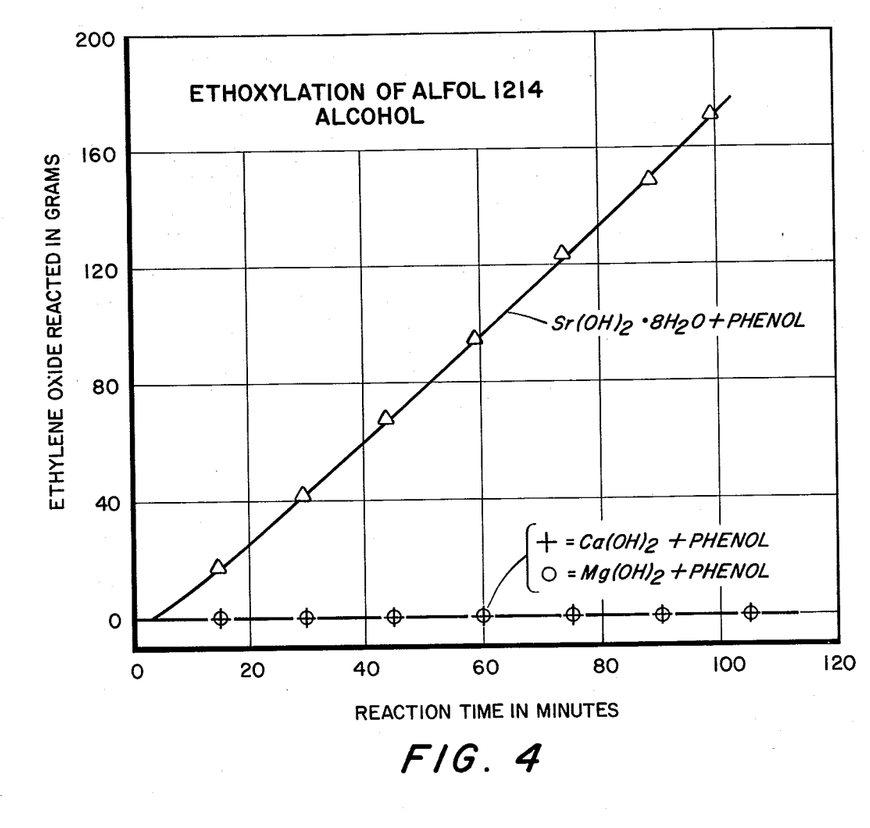

Several comparative experiments were carried out using the procedure described in Example 1. Different catalyst systems were used comprising strontium hydroxide 0.8$H_2O$/phenol, calcium hydroxide/phenol, and magnesium hydroxide/phenol. The results of the experiment showed that only the strontium/phenol system was active clearly showing the unique property of the strontium based catalyst as compared to calcium or magnesium based catalyst. The results of these comparative experiments are shown in FIG. 4.

EXAMPLE 5

Figure 5:
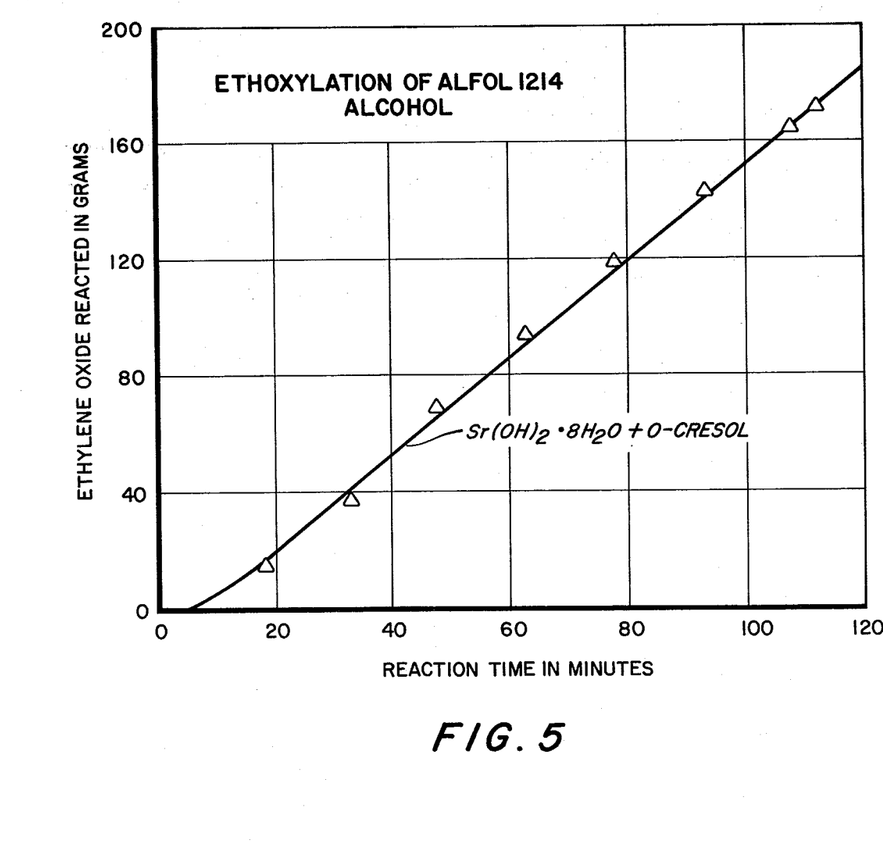

An experiment was carried out as described in Example 1 using 0.5 grams ortho cresol as a co-catalyst in place of phenol. The experiment indicated that ortho cresol also activated the strontium catalyst indicating that various alkylated phenols will act as co-catalysts in the strontium system. This example is a direct comparison to Example 1. The results of the experiment are shown in FIG. 5.

EXAMPLE 6

Distributions of EO and the ethoxylates prepared using different catalysts were determined using high performance liquid chromatography. The results were determined using an experimental procedure as described in Example 1. Comparative examples were carried out using strontium based catalysts as opposed to alkali metal base catalysts, specifically potassium. It was also determined that free alcohol content in the ethoxylate was much lower from strontium base catalysis than that from potassium base catalysis.

Figure 6:
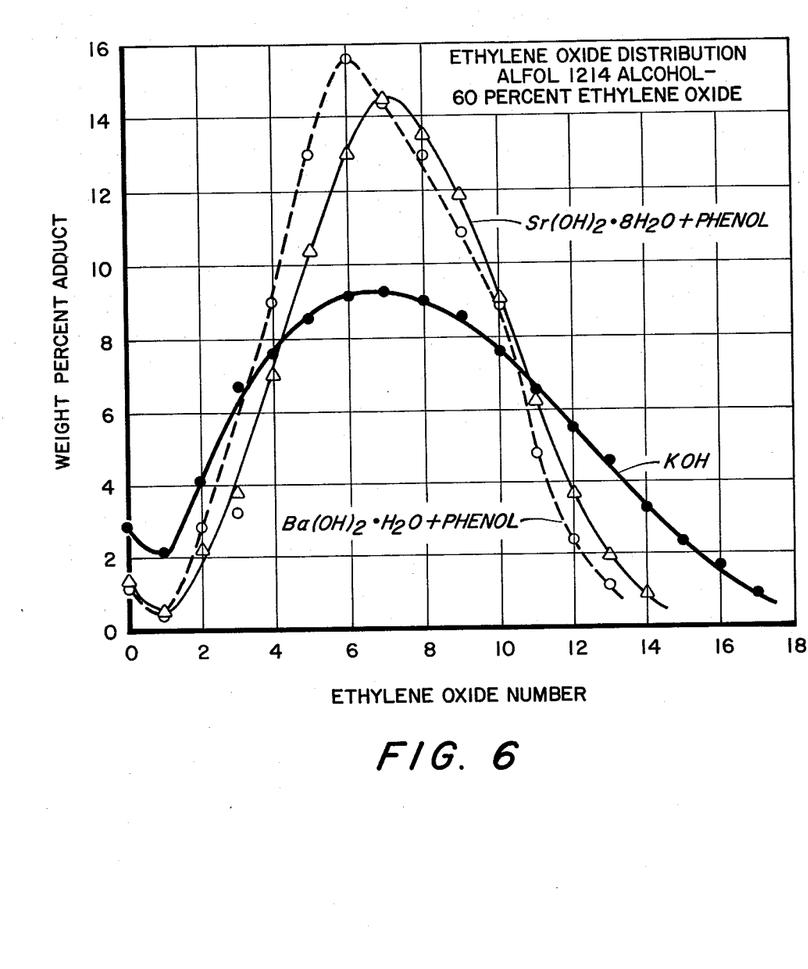

The results of these determinations are shown in FIG. 6, where the weight percent of the adduct is plotted on the vertical axis against the number of EO units incorporated into that adduct as shown on the horizontal axis.

EXAMPLE 7

Figure 7:
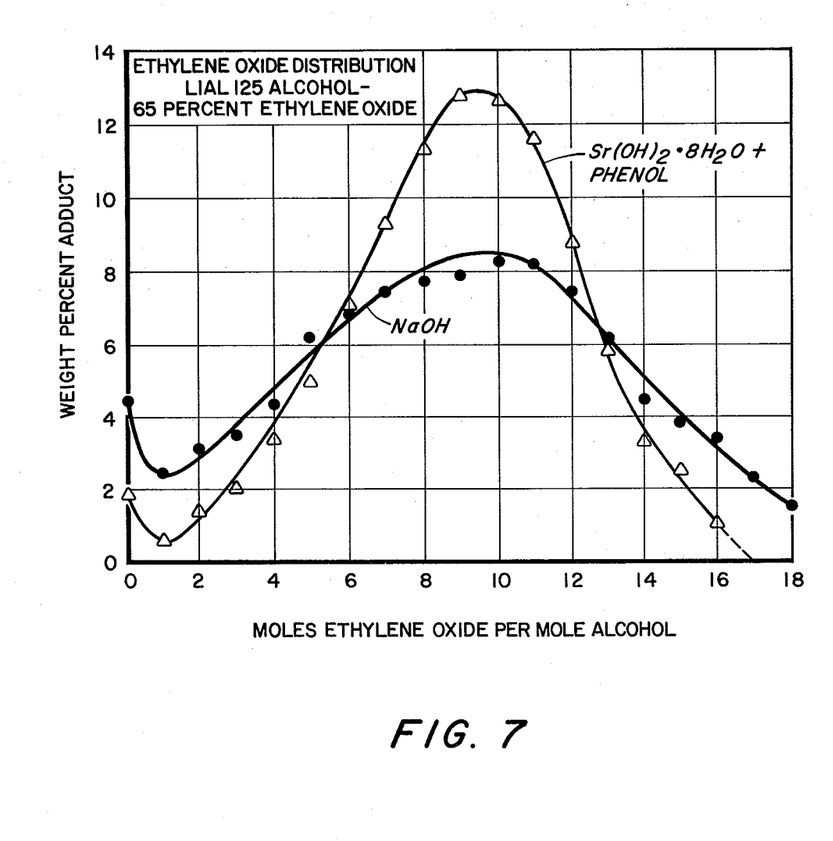
Figure 8:
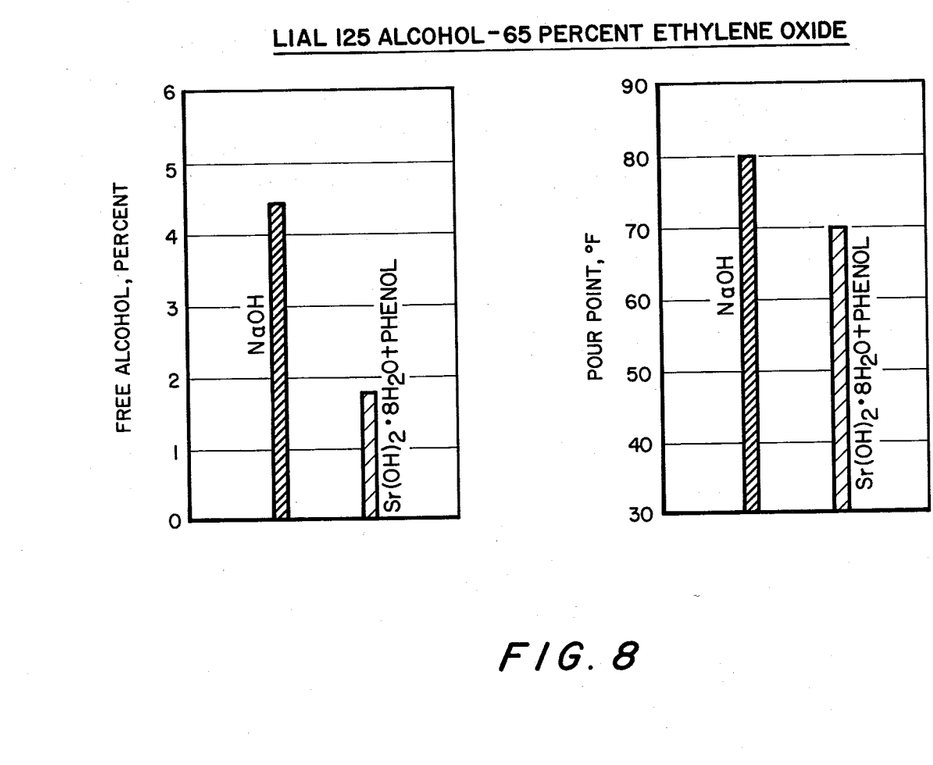

A reactor as described in Example 1 was charged with 105 grams of LIAL 125 alcohol (12 to 15 carbon atom alcohol produced by the oxo process, trademark of and sold by Liquichimica Company, Italy). 0.15 grams of sodium hydroxide catalyst was then added. After purging with nitrogen at 250 cc per minute for 1 hour at 150° C., the reactor was evacuated and the temperature was raised to 170° C. Ethylene oxide was then introduced to a total pressure of about 40 psig and EO uptake of 195 grams was allowed to proceed at this pressure. After ethoxylation, the catalyst was neutralized with acid. Free alcohol, pour point data and ethylene oxide distribution were determined. The results are shown in FIGS. 7 and 8.

EXAMPLE 8

A comparative experiment was performed exactly as described in Example 7 by using 0.6 grams of strontium hydroxide $0.8H_2O$ catalyst and 1 gram of phenol co-catalyst. Carbon dioxide was used to neutralize the catalyst. Ethylene oxide distribution, free alcohol and pour point data were determined. Superior performance of the strontium catalyst as compared to the alkali metal catalyst is clearly shown in FIGS. 7 and 8.

EXAMPLE 9

Figure 9:
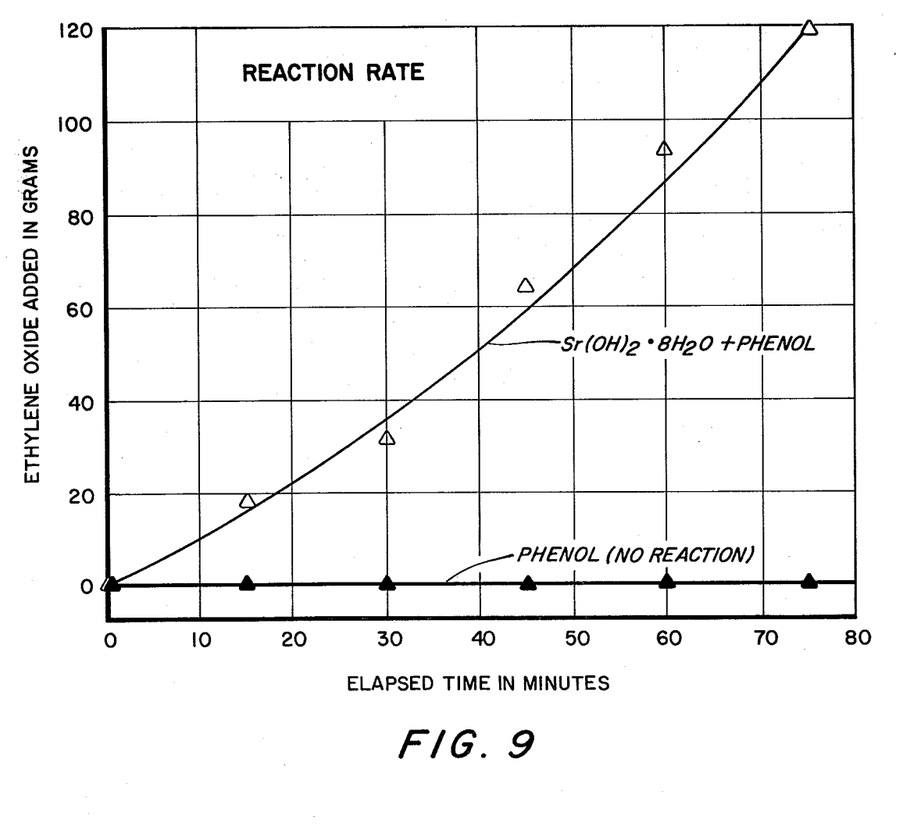

An experiment was carried out as described in Example 8 using 180 grams of LIAL 125 alcohol and 125 grams of ethylene oxide. A comparable experiment was performed using only 2 grams of phenol as a catalyst. The reaction rates as evidenced by EO uptake were determined. The results are shown in FIG. 9 showing that the phenol acts only as a promoter and has no inherent catalytic activity. This comparative example clearly shows a synergistic effect of the phenol or substituted phenol promoters upon the strontium catalysts of the instant invention. The criticality of using the two as a system has been illustrated.

EXAMPLE 10

Figure 10:
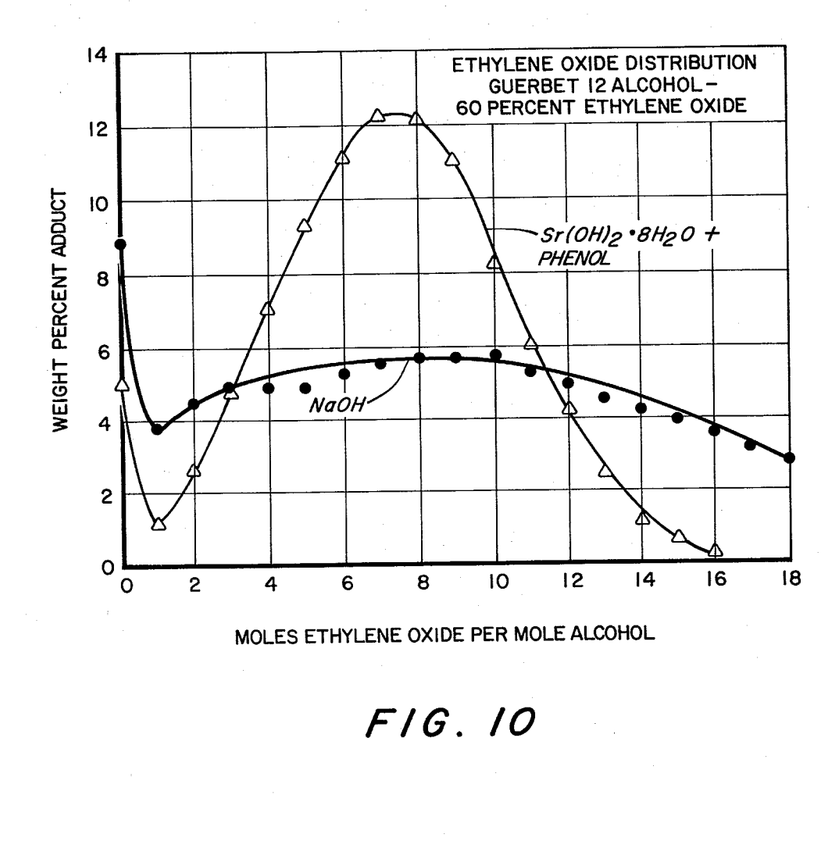
Figure 11:
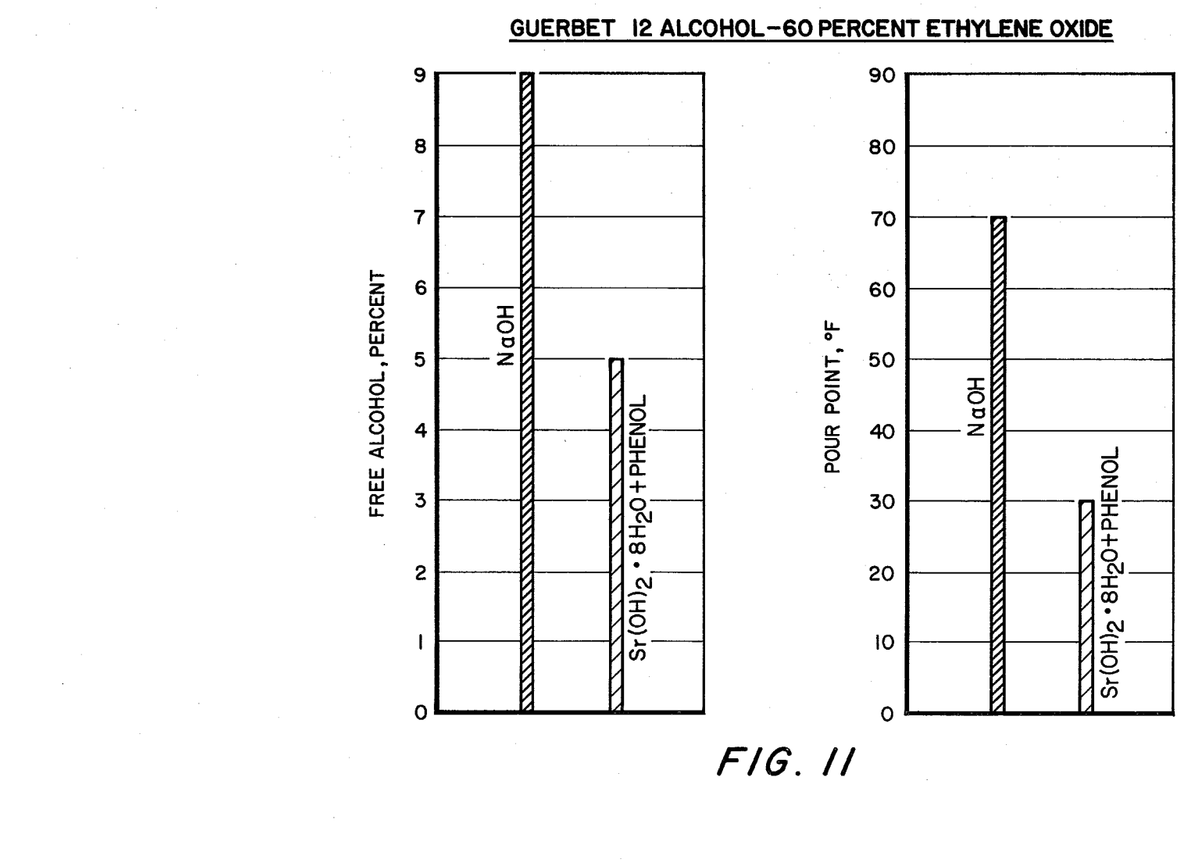

An experiment was carried out as described in Example 8 using 120 grams of branched Guerbet 12 alcohol, produced by the Guerbet process, and 100 grams of ethylene oxide. EO distribution, free alcohol and pour point data were determined. The results are shown in FIGS. 10 and 11.

EXAMPLE 11

A comparative experiment to Example 10 was carried out as described in Example 7 using 120 grams of branched Guerbet alcohols and 120 grams of ethylene oxide. EO distribution, free alcohol and pour point data were determined. The superior performance of the Example 10 strontium catalyst is clearly shown by reference to FIGS. 10 and 11.

Thus the catalyst and method of the instant invention are extremely well suited for the ethoxylation of alcohols produced by hydroformylation (or oxo)/hydrogenation, by Guerbet reactions, and for alcohols produced by aluminum chemistry. Many of these alcohols have in the past presented difficulty when used as reactants for ethoxylation because of the high concentration of unreacted alcohols. However, the catalyst of the instant invention produces extremely good ethoxylates using these alcohols.

The superiority of the strontium base catalyst of the instant invention are evident when viewing the actual samples obtained. At low ethoxylation concentrations, i.e. 30–40%, the barium and strontium catalysts produce water clear ethoxylated material while alkali metal ethoxylates are hazy or cloudy. The difference is much more apparent at high concentration levels, such as 65% ethoxylation, where the alkali metal catalyst ethoxylates are an off-white solid, and the strontium produced ethoxylates are a water clear fluid.

Thus it is apparent that by practicing the instant invention, high mole adduct ethoxylates of alcohols can be obtained in a very narrow, highly desirable distribution range while producing very low amounts of by-products and unreacted free alcohols. In addition, a desirably fast reaction rate and greatly reduced induction period are additional benefits. The gas liquid chromatographic (GLC) analysis of the experiments described indicate that the basic strontium containing catalyst of the instant invention when promoted by phenols or substituted phenols are low in by-products and unreacted free alcohols. A comparison with sodium hydroxide shows these catalyst systems favorably compared to known basic catalyst. Both the strontium/cresylic acid systems and the alkali metal ethoxylation products contain less than 1 part per million (ppm) dioxane and less than 2 weight percent polyethylene glycol based on total reaction product and determined by solvent extraction. These basic catalysts produce reaction products far superior to those obtained with acid catalyzed ethoxylation, these reaction products normally contain dioxane at levels above 1,000 parts per million and polyethylene glycol above 3 weight percent.

Although exemplified as a batch reaction, the catalysts of the instant invention are extremely well suited to continuous reaction methods since the reaction products are of extremely high desirable quality and quantity. The catalysts of the instant invention are normally solid in form.

While certain embodiments and details have been shown for the purpose of illustrating this invention, it will be apparent to those skilled in this art that various changes and modifications may be made herein without departing from the spirit or scope of the invention.

We claim:

1. A method for the ethoxylation of alkanols comprising contacting said alkanols with ethylene oxide in the presence of a catalyst system comprising at least 1 material selected from the group consisting of strontium oxide, strontium hydroxide hydrated strontium hydroxide, together with an effective amount of a phenol or substituted phenol of the general formula wherein $R^1$, $R^2$, $R^3$, $R^4$, and $R^5$ are, independently, hydrogen or an alkyl group containing from 1 to 16 carbon atoms and wherein the ethoxylation is carried out at a temperature of from about 90° to about 260° C.

2. A method as described in claim 1 wherein the catalyst is selected from the group consisting of strontium hydroxide and hydrated strontium hydroxide together with an effective amount of a phenol promoter.

3. A method as described in claim 1 wherein the alkanol to be ethoxylated contains from about 4 to about 24 carbon atoms.

4. A method as described in claim 3 wherein the alcohol is a primary alkanol.

5. A method as described in claim 3 wherein the alkanol is a product of a hydroformylation/hydrogenation reaction.

6. A method as described in claim 1 wherein the reaction is carried out at pressures up to about 100 pounds per square inch gauge.

7. A method as described in claim 6 wherein the ethylene oxide adduct ratio ranges from about 30 weight percent to about 80 weight percent of the ethoxylation product.

8. A method as described in claim 7 wherein the strontium catalyst is present in an amount from about 0.05 to about 5.0 percent by weight based upon the alkanol to be reacted.

9. A method as described in claim 7 wherein the strontium catalyst is present in an amount from about 0.15 to about 2 percent by weight based upon the alkanol to be reacted.

10. A method as described in claim 1 when carried out in a contiuous fashion.

11. A method as described in claim 7 wherein the alkanol is a linear primary alkanol containing from about 8 to about 18 carbon atoms, the ethylene oxide is present in an amount of from about 40 to about 70%, the temperature is about 180° C. the pressure is about 50 psig, and the strontium containing catalyst is present in a concentration of from about 0.05 to about 5.0% based on the weight of the alkanol to be reacted, together with an effective amount of phenol or substituted phenol to effect the ethoxylation.

* * * * *